US012661460B2

(12) United States Patent
Hubert

(10) Patent No.: US 12,661,460 B2
(45) Date of Patent: Jun. 23, 2026

(54) DRUG DELIVERY DEVICES WITH A SPINNING NOZZLE

(71) Applicant: JANSSEN PHARMACEUTICA NV, Beerse (BE)

(72) Inventor: Emma Louise Hubert, San Jose, CA (US)

(73) Assignee: Janssen Pharmaceutica NV, Beerse (BE)

( * ) Notice: Subject to any disclaimer, the term of this patent is extended or adjusted under 35 U.S.C. 154(b) by 658 days.

(21) Appl. No.: 18/024,083

(22) PCT Filed: Aug. 31, 2021

(86) PCT No.: PCT/EP2021/074035
§ 371 (c)(1),
(2) Date: Mar. 1, 2023

(87) PCT Pub. No.: WO2022/049077
PCT Pub. Date: Mar. 10, 2022

(65) Prior Publication Data
US 2023/0270953 A1     Aug. 31, 2023

Related U.S. Application Data

(60) Provisional application No. 63/073,003, filed on Sep. 1, 2020.

(51) Int. Cl.
*A61M 11/00*     (2006.01)
*A61M 15/00*     (2006.01)

(52) U.S. Cl.
CPC ........ *A61M 11/007* (2014.02); *A61M 15/003* (2014.02); *A61M 2206/16* (2013.01)

(58) Field of Classification Search
CPC .............. A61M 11/007; A61M 15/003; A61M 2206/16; A61M 2205/8218; A61M 11/02;
(Continued)

(56) References Cited

U.S. PATENT DOCUMENTS 3,795,244 A * 3/1974 Lax ................... A61M 15/0033
128/203.15
6,398,074 B1   6/2002  Bruna et al.
(Continued)

FOREIGN PATENT DOCUMENTS

WO     WO-99/46055 A1 * 9/1999

OTHER PUBLICATIONS

International Search Report and Written Opinion, received for PCT Application No. PCT/EP2021/074035, mailed on Dec. 7, 2021, 18 pages.

*Primary Examiner* — Theodore J Stigell
(74) *Attorney, Agent, or Firm* — Craig M. Brown

(57)     ABSTRACT

Various exemplary drug delivery devices with a spinning nozzle, drug products utilizing the same, and methods of using drug delivery devices with a spinning nozzle are provided. In general, a nasal drug delivery device configured to dispense a drug therefrom includes a spinning nozzle configured to facilitate the drug's ejection into a patient's nose. The spinning nozzle is located between a drug holder containing the drug to be dispensed and an opening of the drug delivery device through which the drug exits the drug delivery device. The spinning nozzle is configured to spin during the drug's delivery as the drug travels from the drug holder and out of the drug delivery device. The spinning nozzle includes a plurality of perforations therein through which the drug as a liquid is configured to pass. The spinning of the spinning nozzle causes the drug to exit the drug delivery device as a fine mist.

30 Claims, 6 Drawing Sheets

(58) Field of Classification Search
CPC ........ A61M 2202/064; A61M 2206/10; A61M
15/0036; A61M 15/08; A61M 15/004
See application file for complete search history.

(56) References Cited

U.S. PATENT DOCUMENTS

| | | | |
|---|---|---|---|
| 8,820,317 B2 * | 9/2014 | Kern | A61M 15/0085 |
| | | | 239/338 |
| 2010/0258118 A1 * | 10/2010 | Morton | A61M 15/0078 |
| | | | 264/9 |
| 2013/0319412 A1 | 12/2013 | Glynn | |
| 2017/0043109 A1 | 2/2017 | Hoekman et al. | |
| 2018/0361085 A1 | 12/2018 | Malhotra et al. | |

* cited by examiner

DRUG DELIVERY DEVICES WITH A SPINNING NOZZLE

CROSS REFERENCE TO RELATED APPLICATIONS

This application is the U.S. national stage of PCT Application No. PCT/EP2021/074035, filed Aug. 31, 2021, which claims priority to U.S. Provisional Patent Application No. 63/073,003, filed Sep. 1, 2020, the entire contents of each of which are hereby incorporated by reference as if set forth in their entirety herein.

FIELD

The present disclosure relates generally to a drug delivery device with a spinning nozzle and drug products utilizing the same.

BACKGROUND

There are many different ways in which a drug can be administered to a user. Depending on the drug, intranasal drug delivery can be one of the most effective ways to achieve desired clinical benefits in a timely manner and in a manner that is convenient and comfortable for a patient.

Intranasal drug administration is a non-invasive route for drug delivery. Since the nasal mucosa offers numerous benefits as a target tissue for drug delivery, a wide variety of drugs may be administered by intranasal systemic action. Moreover, intranasal drug delivery can avoid the risks and discomfort associated with other routes of drug delivery, such as intravenous drug delivery, and can allow for easy self-administration.

Generally, to maximize the efficacy of the drug through intranasal administration, the majority volume of the aerosolized dose of the drug needs to reach the correct region of the nasal cavity. As such, additional measures may need to be taken for effective intranasal drug delivery. For example, the user may need to have a clear nostril, tilt their head back at approximately 45°, close the opposite nostril, and then sniff gently while the dose of drug is administered. In order to coordinate these measures, and given that nasal administration is intimate, self-administration by the user may be desired. Further, due to the nasal cycle (alternating physiological partial congestion of the nasal turbinate to facilitate nasal function) or pathological congestion, one nostril is likely to provide a more effective drug delivery route than the other nostril at any given time. As such, it is desired that an equal dose of the drug be delivered to each nostril of the user to inhibit under-dosing of the drug.

Dual-dose intranasal drug delivery devices are available that are designed for self-administration of two distinct aerosolized sprays, one for each nostril, that together constitute one dose of drug. These devices require a series of operational steps that the user needs to properly carry out to effect optimal drug delivery through self-administration. However, the majority volume of the aerosolized dose of the drug does not always reach the correct region of a patient's nasal cavity because the drug is not sufficiently aerosolized. In such instances, the patient does not receive the full intended drug dose, which may adversely affect the patient's health and/or may require an additional drug delivery that is inconvenient and/or that could result in the patient receiving too much of the drug.

Accordingly, there remains a need for improved nasal drug delivery devices.

SUMMARY

In general, a drug delivery device with a spinning nozzle, drug products utilizing the same, and methods of using a drug delivery device with a spinning nozzle are provided.

In one aspect, a drug delivery device is provided that in one embodiment includes a tip configured to be positioned in a nose of a patient. The tip has an opening therein. The drug delivery device also includes a drug holder with an air chamber, a drug chamber, a first seal member that isolates the air chamber from the opening, and a second seal member that isolates the air chamber from the drug chamber. The air chamber contains air therein. The drug chamber contains a drug therein. The drug delivery device also includes a turbine located distal to the opening and proximal to the air chamber. The breaking of the first seal member is configured to cause the air to flow proximally and thereby cause the turbine to spin, and the breaking of the second seal member is configured to cause the drug to be drawn proximally and pass through the turbine and then out of the opening.

The drug delivery device can vary in any number of ways. For example, the drug delivery device can include a piercing element in fluid communication with the opening and configured to break the first seal member and to subsequently break the second seal member. The piercing element can include a tubular needle, and in at least some embodiments, the turbine can be located in a hollow interior of the tubular needle. In at least some embodiments, the turbine can be located proximal to the piercing element and distal to the opening. In at least some embodiments, the drug delivery device can include an actuator configured to be actuated to cause the needle to break the first seal member and subsequently break the second seal member. The drug delivery device can include a dispensing head that includes the tip, and the actuator can include a body that seats the drug holder therein and that is seated in a socket of the dispensing head.

For another example, the turbine can include a plurality of vanes extending radially outward from a center point of the turbine, perforations can be formed in the vanes, the drug is configured pass through the perforations, and the turbine can be configured to spin about the center point. For still another example, the turbine can include a pinwheel. For another example, the drug holder can include a vial.

For yet another example, the drug can be one of ketamine, esketamine, naloxone, and sumatriptan.

In another aspect, a drug product is provided that in one embodiment includes a drug product disposed in a drug delivery device. The drug delivery device includes a tip configured to be positioned in a nose of a patient. The tip has an opening therein. The drug delivery device also includes a drug holder with an air chamber, a drug chamber, a first seal member that isolates the air chamber from the opening, and a second seal member that isolates the air chamber from the drug chamber. The air chamber contains air therein. The drug chamber contains the drug product therein. The drug delivery device also includes a perforated turbine located distal to the opening and proximal to the air chamber. The breaking of the first seal member is configured to cause the air to flow proximally and thereby cause the turbine to spin, and the breaking of the second seal member is configured to cause the drug product to be drawn proximally and pass through the perforations of the turbine and then out of the opening. The drug product is one of ketamine, esketamine, naloxone, and sumatriptan. The drug delivery device can have any number of variations.

In another embodiment, a drug delivery device includes a tip configured to be positioned in a nose of a patient The tip has an opening therein. The drug delivery device also includes an air chamber containing air therein, and a nozzle located distal to the opening and proximal to the air chamber. The nozzle includes a plurality of perforations therethrough. The drug delivery device also includes a first seal member located between the air chamber and the opening and providing a seal therebetween, a drug chamber containing a drug therein and located distal to the air chamber, a second seal member located between the air chamber and the drug chamber and providing a seal therebetween, and an actuator configured to be actuated to cause the first seal member to break and subsequently cause the second seal member to break. The breaking of the first seal member is configured to cause the air to flow proximally and thereby cause the nozzle to spin, and the breaking of the second seal member is configured to cause the drug to be drawn proximally and pass through the perforations and then out of the opening.

The drug delivery device can vary in any number of ways. For example, the drug delivery device can include a piercing element in fluid communication with the opening and configured to, in response to the actuation of the actuator, break the first seal member and to subsequently break the second seal member. The piercing element can include a tubular needle, and in at least some embodiments, the nozzle is located in a hollow interior of the tubular needle. In at least some embodiments, the nozzle can be located proximal to the piercing element and distal to the opening.

For another example, the drug delivery device can include a dispensing head that includes the tip, and the actuator can include a body that is seated in a socket of the dispensing head.

For yet another example, the nozzle can include a plurality of vanes extending radially outward from a center point of the nozzle, the perforations can be formed in the vanes, and the nozzle can be configured to spin about the center point.

For still another example, the drug can be one of ketamine, esketamine, naloxone, and sumatriptan.

In another aspect, a drug product is provided that in one embodiment includes a drug product disposed in a drug delivery device. The drug delivery device includes a tip configured to be positioned in a nose of a patient The tip has an opening therein. The drug delivery device also includes an air chamber containing air therein, and a nozzle located distal to the opening and proximal to the air chamber. The nozzle includes a plurality of perforations therethrough. The drug delivery device also includes a first seal member located between the air chamber and the opening and providing a seal therebetween, a drug chamber containing the drug product therein and located distal to the air chamber, a second seal member located between the air chamber and the drug chamber and providing a seal therebetween, and an actuator configured to be actuated to cause the first seal member to break and subsequently cause the second seal member to break. The breaking of the first seal member is configured to cause the air to flow proximally and thereby cause the nozzle to spin, and the breaking of the second seal member is configured to cause the drug product to be drawn proximally and pass through the perforations and then out of the opening. The drug product is one of ketamine, esketamine, naloxone, and sumatriptan. The drug delivery device can have any number of variations.

In another aspect, a drug delivery method is provided that in one embodiment includes breaking a first seal member of a nasal drug delivery device and thereby causing air located in the drug delivery device to flow proximally. The proximal flow of the air causes a turbine of the drug delivery device to spin. The drug delivery method also includes, after breaking the first seal member and after the turbine has begun to spin, breaking a second seal member of the drug delivery device and thereby causing a drug to be drawn proximally by the proximal flow of the air, to then pass through the spinning turbine, and to then exit the drug delivery device through an opening in the drug delivery device.

The drug delivery method can vary in any number of ways. For example, a drug holder can include an air chamber located distal to the first seal member and proximal to the second seal member such that breaking the first seal member allows air in the air chamber to flow proximally, and the drug holder can include a drug chamber located distal to the second seal member such that breaking the second seal member allows drug in the drug chamber to be drawn proximally.

For another example, a piercing element of the drug delivery device can break the first seal member and subsequently break the second seal member, and in at least some embodiments, the air flowing proximally can pass through a hollow interior of the piercing element. In at least some embodiments, the air flowing proximally can pass through perforations formed in the turbine before exiting the hollow interior of the piercing element. In at least some embodiments, the air flowing proximally can exit the hollow interior of the piercing element before passing through the perforations of the turbine.

For yet another example, breaking the first seal member and breaking the second seal member can include actuating an actuator of the drug delivery device. In at least some embodiments, the actuator can include a body of the drug delivery device that is seated in a socket of a dispensing head of the drug delivery device.

For another example, the turbine can include a pinwheel. For yet another example, the drug holder can include a vial. For still another example, the drug can be one of ketamine, esketamine, naloxone, and sumatriptan.

BRIEF DESCRIPTION OF DRAWINGS

The present invention is described by way of reference to the accompanying figures which are as follows.

DETAILED DESCRIPTION

Figure 1:
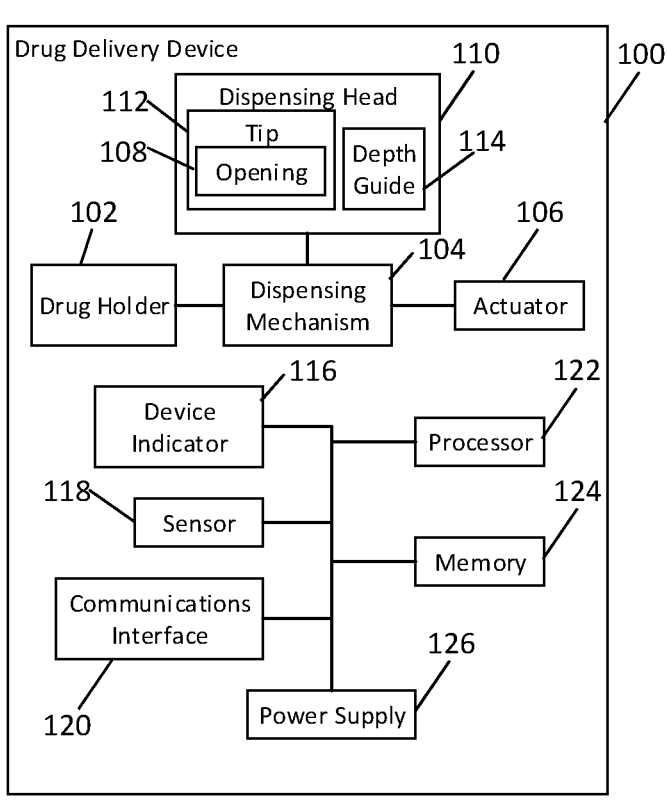
FIG. 1 is a block diagram of one embodiment of a drug delivery device.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary drug delivery devices with a spinning nozzle, drug products utilizing the same, and methods of using drug delivery devices with a spinning nozzle are provided. In general, a nasal drug delivery device configured to dispense a drug therefrom includes a spinning nozzle configured to facilitate the drug's ejection into a patient's nose. The spinning nozzle is located between a drug holder containing the drug to be dispensed and an opening of the drug delivery device through which the drug exits the drug delivery device. The spinning nozzle is thus configured to allow the drug to pass through the spinning nozzle as the drug travels from the drug holder and out of the drug delivery device. The spinning nozzle is configured to spin during the drug's delivery as the drug travels from the drug holder and out of the drug delivery device. The spinning nozzle includes a plurality of perforations therein, e.g., holes or openings formed therethrough, through which the drug as a liquid is configured to pass. The spinning of the spinning nozzle causes the drug to exit the drug delivery device as a fine mist in which the drug is dispersed as liquid particles of a substantially same size and at a substantially consistent distribution as the drug exits the drug delivery device through the opening. The drug being dispersed as liquid particles of a substantially same size and being at a substantially consistent distribution may help the drug reach the correct region of a patient's nasal cavity because the drug is sufficiently aerosolized. The patient may therefore be more likely to receive the full intended drug dose and thus not require an additional drug delivery that is inconvenient and/or that could result in the patient receiving too much of the drug.

The drug to be delivered using a drug delivery device as described herein can be any of a variety of drugs. Examples of drugs that can be delivered using a drug delivery device as described herein include antibodies (such as monoclonal antibodies), hormones, antitoxins, substances for the control of pain, substances for the control of thrombosis, substances for the control of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying anti-rheumatic drugs, erythropoietin, and vaccines. Examples of drugs that can be delivered using a drug delivery device as described herein include ketamine (e.g., Ketalar®), esketamine (e.g., Spravato®, Ketanest®, and Ketanest-S®), naloxone (e.g., Narcan®), and sumatriptan (e.g., Imitrex®).

FIG. 1 illustrates one embodiment of a drug delivery device 100 that includes a spinning nozzle and that is configured to expel a drug into a nose of a patient. As will be appreciated by a person skilled in the art, the drug delivery device 100 can include different features in different embodiments depending upon various requirements, such as the type of drug, typical dosage(s) of the drug, safety requirements in various jurisdictions, whether the device is powered, etc.

The drug delivery device 100 includes a drug holder 102 configured to contain a drug therein for delivery from the device 100 to a patient. The drug holder 102 can have a variety of configurations, such as a cartridge, a vial, a blow-fill-seal (BFS) capsule, etc. In an exemplary embodiment, the drug holder 102 is a vial. An exemplary vial is formed of one or more materials, e.g., glass, polymer(s), etc. In some embodiments, a vial can be formed of glass. In other embodiments, a vial can be formed of one or more polymers. In yet other embodiments, different portions of a vial can be formed of different materials.

Figure 2:
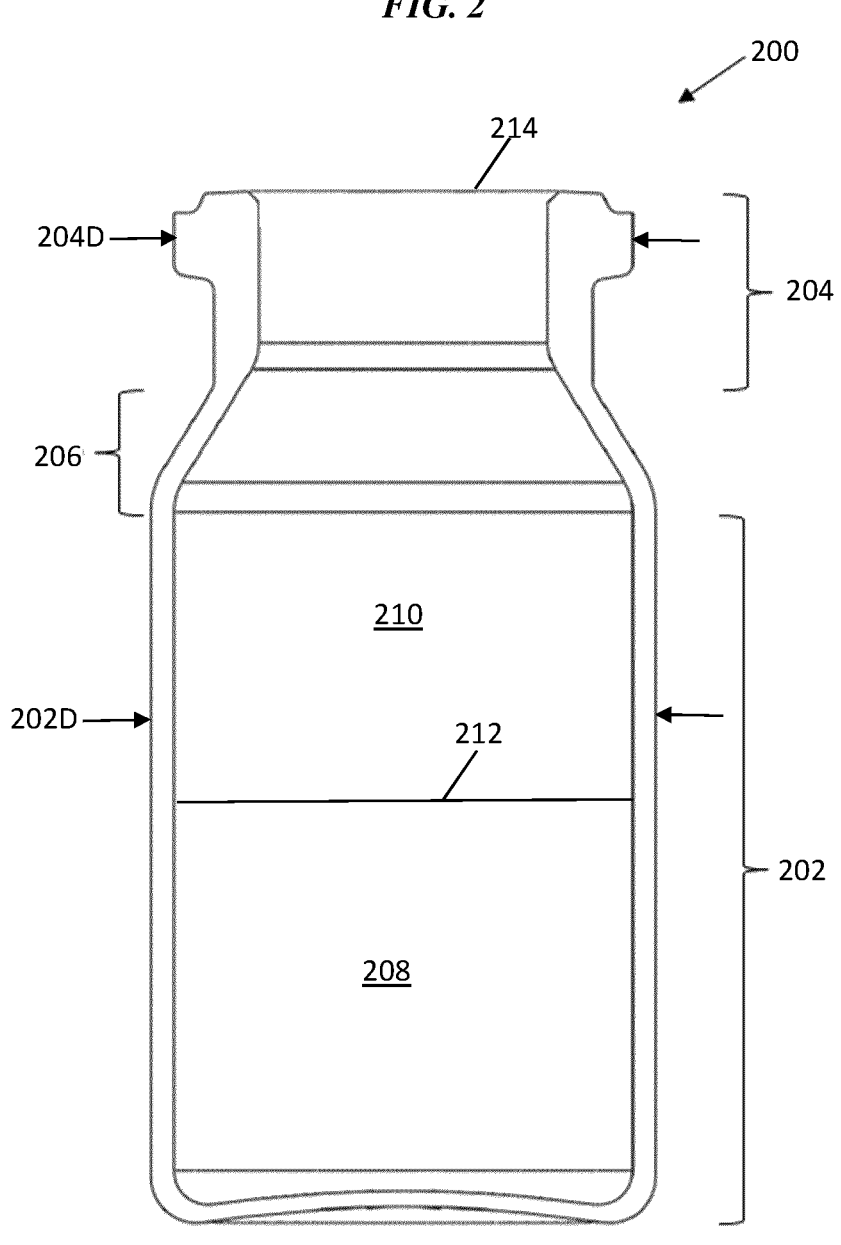
FIG. 2 is a side cross-sectional view of one embodiment of a vial.

FIG. 2 illustrates an exemplary embodiment of the drug holder 102 in the form of a vial 200 configured to contain a drug therein. The vial 200 includes a base or distal portion 202 and a head or proximal portion 204. As shown, the vial 200 also includes an inwardly tapering neck portion 206 that extends between the base portion 202 and the head portion 204. The inwardly tapering neck portion 206 allows the head portion 204 to have a maximum outer diameter 204D that is less than a maximum outer diameter 202D of the base portion 202. In other embodiments, the taper between the base and head portions 202, 204 can be omitted, and the base and head portions 202, 204 can have a same maximum outer diameter 202D, 204D as one another.

The base portion 202 defines a distal cavity 208 within the base portion 202 that is configured to contain the drug therein. The base portion 202 also defines a proximal cavity 210 within the base portion 202 that is configured to contain air therein.

The vial 200 includes a first seal member 214 configured to provide a fluid tight seal at a proximal end of the proximal cavity 210 such that the air is contained in the proximal cavity 210 in the vial 200 until the seal provided by the first seal member 214 is broken. The first seal member 214 is located in the head portion 204 of the vial 200 in this illustrated embodiment but can instead be located in the base portion 202. The seal provided by the first seal member 214 can be broken in a variety of ways, such as by being pierced by a needle, pin, piston, etc. of the drug delivery device to which the vial 200 is coupled. The first seal member 214 can have a variety of configurations, as will be appreciated by a person skilled in the art, such as by being a pierceable polymer septum or a foil layer. The first seal member 214 can be protected from accidental puncturing or piercing before intended use with a removable protective member or stopper, such as a tamper evident (TE) seal, etc. located at the proximal end of the vial 200.

The distal and proximal cavities 208, 210 are isolated from one another in an initial state of the vial 200. The vial 200 includes a second seal member 212 that is located in the base portion 202. The second seal member 212 is configured to provide a fluid tight seal such that the drug in the distal cavity 208 and the air in the proximal cavity 210 are separated from each other until the seal provided by the second seal member 212 is broken. The seal provided by the second seal member 212 can be broken in a variety of ways, such as by being pierced by a needle of the drug delivery device to which the vial 200 is coupled, such as the same needle that breaks the first seal member 214. The second seal member 212 can have a variety of configurations, as will be appreciated by a person skilled in the art, such as by being a pierceable polymer septum or a foil layer.

While the base portion 202 can have a variety of configurations, in this illustrated embodiment, the base portion 202 has a substantially cylindrical shape. In other embodiments, the base portion 202 can have any other suitable shapes, e.g., a substantially rectangular shape, etc. A person skilled in the art will appreciate that a shape may not be a precise shape (e.g., a precise cylinder or a precise rectangle) but nevertheless be considered to be substantially that shape due to any number of factors, such as manufacturing tolerances and sensitivity of measurement equipment.

An exemplary vial can include a variety of features to facilitate sealing and storing a drug therein, as described herein and illustrated in the drawings. However, a person skilled in the art will appreciate that the vials can include only some of these features and/or can include a variety of other features known in the art. The vials described herein are merely intended to represent certain exemplary embodiments.

Referring again to FIG. 1, the drug delivery device 100 also includes a dispensing mechanism 104 that is operatively coupled to the drug holder 102 and configured to drive the drug out of device 100 from the drug holder 102. The dispensing mechanism 104 in this illustrated embodiment includes the spinning nozzle. The spinning nozzle can have a variety of configurations, as discussed further below. The dispensing mechanism 104 can include additional component(s). For example, the dispensing mechanism 104 can include a plunger configured to be driven by the propellant to push the drug out of the drug holder 102.

The drug delivery device 100 also includes an actuator 106 configured to be actuated by a user to cause the dispensing mechanism 104 to begin delivering a dose of the drug through an opening 108 in the drug delivery device 100. In an exemplary embodiment, the drug delivery device 100 is configured to be self-administered such that the user who actuates the actuator 106 is the patient receiving the drug from the drug delivery device 100. The actuator 106 can have a variety of configurations, as discussed further below. For example, the actuator 106 can include a pressable button. For another example, the actuator 106 can include a movable switch. For yet another example, the actuator 106 can include a squeezable body of the drug holder 102.

The opening 108 through which the drug exits the drug delivery device 100 is formed in a dispensing head 110 of the drug delivery device 100 in a tip 112 of the dispensing head 110. The tip 112 is configured to be inserted into a nostril of a patient. The dispensing head 110 includes a depth guide 114 configured to contact skin of the patient, e.g., between the patient's first and second nostrils, such that a longitudinal axis of the dispensing head 110 is substantially aligned with a longitudinal axis of the nostril in which the tip 112 is inserted. A person skilled in the art will appreciate that the longitudinal axes may not be precisely aligned but nevertheless be considered to be substantially aligned due to any number of factors, such as manufacturing tolerances and sensitivity of measurement equipment.

In an exemplary embodiment, the dispensing head 110 has a tapered shape in which the dispensing head 110 has a smaller diameter at its distal end than at its proximal end where the opening 108 is located. The opening 108 having a relatively small diameter facilitates spray of the drug out of the opening 108, as will be appreciated by a person skilled in the art. A spray chamber through which the drug is configured to pass before exiting the opening 108 is located within a proximal portion of the tapered dispensing head 110, distal to the opening 108. When the drug passes through the spray chamber at speed, the spray chamber facilitates production of a fine mist that exits through the opening 108 with a consistent spray pattern.

In some embodiments, the dispensing head 110 can include two tips 112 each having an opening 108 therein such that the drug delivery device 100 is configured to simultaneously deliver doses of drug into two nostrils in response to a single actuation of the actuator 106.

The spinning nozzle may not be part of the dispensing head 110. For example, the spinning nozzle can be located distal to the dispensing head 110 in a body of the drug delivery device 100. The spinning nozzle being located distal to the dispensing head 110, and thus distal to the tip 112, may help prevent a patient with the tip 112 inserted into their nose from feeling a vibration of the drug delivery device 100 in their nose, due to the spinning of the spinning nozzle, that the patient is not used to feeling. The spinning nozzle can, however, be located in the dispensing head 110. The spinning nozzle being located in the dispensing head 110 may facilitate the drug being distributed evenly in the tip 112 before exiting through the opening 108. The spinning nozzle being located in the dispensing head 110 may allow the drug to exit through the opening 108 at a higher velocity than if the spinning nozzle were located at a more distal location, e.g., farther away from the opening 108, since the spinning nozzle is configured to accelerate the drug's proximal movement due to the spinning action of the nozzle. Thus, the closer the spinning nozzle is to the opening 108, the faster the drug may be expelled into the patient's nose, which may help the drug travel to the correct region of the nasal cavity.

In embodiments in which the spinning nozzle is located in the dispensing head and the dispensing head 110 includes two tips 112, the drug delivery device 100 can include a single spinning nozzle that is located distal to each of the two tips 112, or the drug delivery device 100 can include a first spinning nozzle located in one of the tips 112 and a second spinning nozzle located in the other one of the tips 112.

The drug delivery device 100 also includes a device indicator 116 configured to present information to a user about a status of the drug delivery device 100 and/or the drug contained in the drug holder 102. The device indicator 116 can be a visual indicator, such as a display screen, one or more lights, one or more colored and/or numbered markings, etc. Alternatively or in addition, the device indicator 116 can be an audio indicator configured to provide sound.

The drug delivery device 100 also includes a sensor 118 configured to sense information relating to the drug delivery device 100 and/or the drug contained in the drug holder 102. Examples of information that the sensor 118 can sense include environmental conditions (e.g., temperature, humidity, geographic location, time, etc.) and spinning nozzle conditions (e.g., whether or not the spinning nozzle is spinning, a speed at which the spinning nozzle is spinning, a start time of the spinning nozzle's spinning, a stop time of the spinning nozzle's spinning, etc.). Sensing spinning nozzle conditions may help ensure that the spinning nozzle is functioning properly and/or aid in confirming that drug delivery occurred. The spinning nozzle conditions can be sensed using any of a variety of sensors, such as a motion sensor configured to sense motion of the spinning nozzle and thereby indicate whether or not the spinning nozzle is spinning, a Hall effect sensor configured to sense displacement of the spinning nozzle and thereby indicate whether or not the spinning nozzle is spinning, a liquid sensor configured to sense presence of liquid proximal to the spinning nozzle and thereby indicate whether or not the spinning nozzle is spinning with liquid drug passing therethrough, an accelerometer configured to sense a speed of spin of the spinning nozzle, a clock or timer configured to track time that can be correlated with other sensed data, etc.

The drug delivery device 100 can also include a communications interface 120 configured to communicate externally data which has been gathered by the sensor 118 about the drug delivery device 100 and/or the drug contained in the drug holder 102, which may facilitate analysis regarding the patient's treatment, patient compliance, use of the drug delivery device 100, etc.

In embodiments in which the drug delivery device 100 includes one or more electrical components, e.g., the device indicator 116 (which in some embodiments can be powered while in other embodiments not be powered), the sensor 118, the communications interface 120, a processor 122, a memory 124, etc., the drug delivery device 100 includes a power supply 126 configured to deliver electrical power to the one or more electrical components of the drug delivery device 100. The power supply 126 can be a source of power which is integral to drug delivery device 100 and/or can be a mechanism configured to connect the drug delivery device 100 to an external source of power. The processor 122 is configured to receive gathered data from the sensor 118 and to cause the data to be stored in the memory 124, to be indicated on the device indicator 110, and/or and to be communicated externally via the communications interface 120. The memory 124 is configured to store instructions that are configured to be executed by the processor 122 for the processor 122 to process information regarding the various electrical components with which the processor 122 is in communication.

As mentioned above, the drug delivery device 100 can include different features in different embodiments depending upon various requirements. For example, the drug delivery device 100 can omit any one or more of the depth guide

114, the device indicator 116, the sensor 118, the communications interface 120, the processor 122, the memory 124, and the power supply 126.

Figure 3:
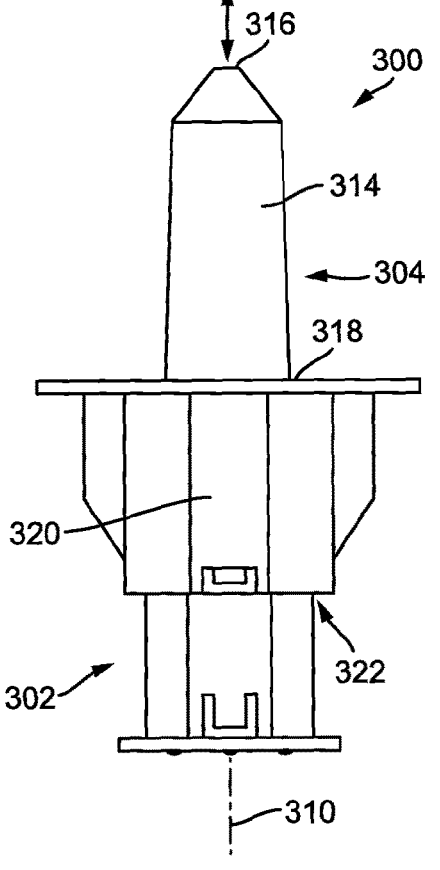
FIG. 3 is a side view of one embodiment of the drug delivery device of FIG. 1, the drug delivery device being in an initial configuration.
Figure 4:
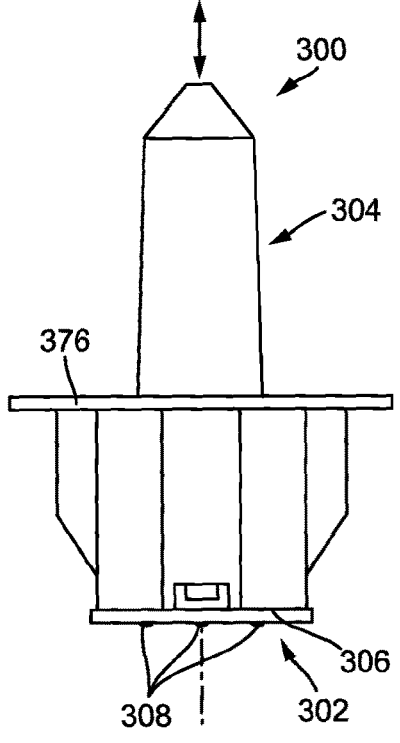
FIG. 4 is a side view of the drug delivery device of FIG. 3, the drug delivery device being in an actuated configuration.

FIGS. 3 and 4 illustrate an exemplary embodiment of the drug delivery device 100 of FIG. 1. FIG. 3 shows this illustrated embodiment of a drug delivery device 300 in an initial or pre-use configuration, and FIG. 4 shows the drug delivery device 300 in an actuated or post use configuration. In the post use configuration, a body 302 of the drug delivery device 300 has been inserted into a dispensing head 304 of the drug delivery device 300 such that only an endplate 306 of the body 302 is visible. The body 302 is configured to be inserted into the dispensing head 304 substantially along a first axis 310. A person skilled in the art will appreciate that the body 302 may not be inserted precisely along the first axis 310 but nevertheless be considered to be inserted substantially along the first axis 310 due to any number of factors, such as manufacturing tolerances and sensitivity of measurement equipment.

The body 302 defines an actuator of the drug delivery device 300 that is configured to be manually moved by a user to be inserted into the dispensing head 304 and cause drug delivery. The endplate 306 includes a gripping feature 308 configured to facilitate actuation by increasing grip of the body's surface for a finger of a user. The gripping feature 308 includes surface projections in this illustrated embodiment but can have other configurations, such as a textured surface, a finger depression, etc.

Figure 5:
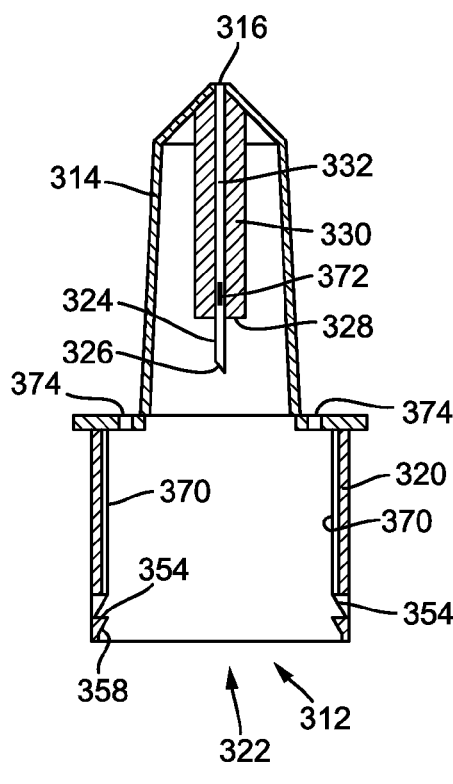
FIG. 5 is a side cross-sectional view of a portion of the drug delivery device of FIG. 3.

As shown in FIG. 5, the dispensing head 304 defines a socket 312 into which the body 302 is configured to be inserted. The dispensing head 304 includes a tip 314 with an opening 316 therein. A base end 318 (see FIG. 3) of the tip 314 is attached to a base portion 320 of the dispensing head 304 that includes a distal opening 322 of the socket 312. A piercing element 324, e.g., a hollow needle, etc., is located in the dispensing head 304 in the tip 314 thereof. The piercing element 324 includes a distal piercing tip or inlet 326 and extends into the socket 312 from a piercer stop 328 of a holder 330 that holds the piercer element 324 within the socket 312. The piercer inlet 326 is in fluid communication with the opening 316 by a conduit or inner lumen 332 or the piercing element 324.

Figure 6:
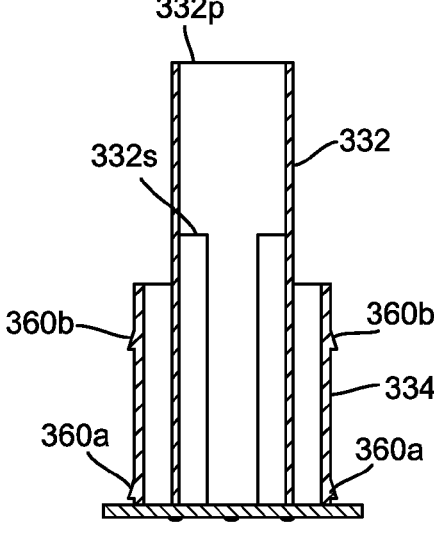
FIG. 6 is a side cross-sectional view of another portion of the drug delivery device of FIG. 3.

As shown in FIG. 6, the body 302 includes a tower 332 within which a drug holder is held, such as the drug holder 200 of FIG. 2. The tower 332 extends from the endplate 306 and is surrounded in a distal portion thereof, e.g., a portion thereof closest to the endplate 306, by a peripheral wall 334. The peripheral wall 334 is spaced apart from and completely surrounds a base of the tower 332. The tower 332 and the peripheral wall 334 extend from the endplate 306 substantially parallel with the first axis 310. A person skilled in the art will appreciate that the tower 332 and the peripheral wall 334 may not be extend precisely parallel with the first axis 310 but nevertheless be considered to extend substantially parallel with the first axis 310 due to any number of factors, such as manufacturing tolerances and sensitivity of measurement equipment. In an exemplary embodiment, the peripheral wall 334 extends from the endplate 306 in a range of about 30% to about 70% of a height of the tower 332. The peripheral wall also includes a first movable arm 360a and a second movable arm 360b.

As shown in FIG. 6, within the tower 332 there is a stop 332s such that when a drug holder 336 is inserted into an open proximal end 332p of the tower 332, the drug holder 336 will rest on the stop 332s. The drug holder 336 can include a shoulder, flange, or other feature at its distal end configured to prevent the drug holder 336 being inserted into the tower 332 incorrectly, e.g., upside-down. In some embodiments, the drug holder 336 is pre-loaded into the tower 332.

Various other aspects of the drug delivery device 300 are further described in U.S. Pat. Pub. No. 2018/0361085 entitled "Nasal Spray Assembly" published Dec. 20, 2018, which is hereby incorporated by reference in its entirety.

Figures 7, 8:
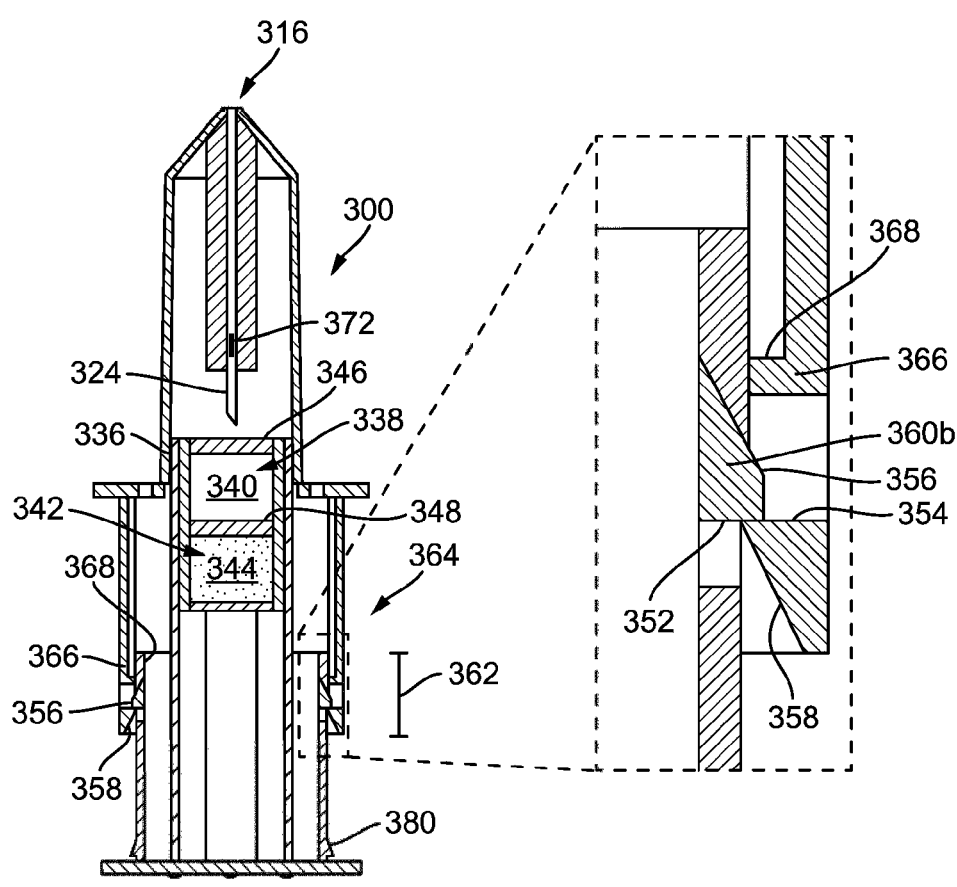
FIG. 7 is a side cross-sectional view of the drug delivery device of FIG. 3.
FIG. 8 is a side cross-sectional view of the drug delivery device of FIG. 4.

FIGS. 7 and 8 illustrate a method of using the drug delivery device 300. As shown in FIG. 7, a drug holder 336 is loaded into the tower 332 of the body 302, and the body 302 is inserted into the socket 312 of the dispensing head 304 along the first axis 310. The drug holder 336 in this illustrated embodiment is generally configured and used similar to the drug holder 200 of FIG. 2 and includes a proximal cavity 338 containing air 340 therein, a distal cavity 342 containing a drug 344 therein, a first seal member 346, and a second seal member 348. The peripheral wall 334 of the body 302 cooperates with the socket 312 to rotationally align the body 302 and the dispensing head 304 about the first axis 310 so that body shoulders 350, 352 of the body 302 and a head shoulder 354 (see FIG. 5) of the dispensing head 304 are aligned along the first axis 310. In other embodiments, the dispensing head 304 includes two separate head shoulders and provides the same functionality, but it is more efficient to have the same head shoulder 354 of the dispensing head 304 used for both pre-lock in the device's initial configuration and post-lock in the device's actuated configuration.

Each of the shoulders 352, 354 is preceded in the direction of relative travel during insertion by a ramp 356, 358 respectively. Once aligned about the first axis 310, the body 302 is inserted into the dispensing head 304 along the first axis 310 until the ramps 356, 358 make contact. Further insertion of the body 302 is made possible by the displacement of the body shoulder 352. The displacement results from resilient deformation of the second movable arm 360b, which carries the body shoulder 352, and is caused by the ramps 356, 358 sliding past one another.

Once the body 302 has travelled a first pre-determined distance 362 into the socket 312, the body shoulder 352 moves beyond the head shoulder 354 in the proximal direction of insertion and the resiliently deformable arm 360b returns to its rest position, and the engagement of the body and head shoulders 352, 354 substantially prevent withdrawal. The body and head shoulders 352 and 354 therefore combine to provide a first function of a pre-lock 364 which automatically engages.

In the pre-use configuration shown in FIG. 7, the pre-lock 364 is engaged. The pre-lock also includes a barrier 366, in this embodiment a ridge 368 in the dispensing head 304 projecting into a recess 370 (see FIG. 5) beyond the head shoulder 354 in the proximal direction of insertion. The ridge 368 and the ramp 356 of the movable arm 360b interact as set out for the interaction of the movable arm 360b and the head shoulder 354, except that the ridge 368 does not include a preceding ramp and therefore the insertion force required to move the second shoulder 352 beyond the ridge 368 is higher than the force required to move it past the head shoulder 354. This provides a threshold force that prevents further insertion, and this force can be varied by altering the size of the ridge 368 in a direction substantially perpendicular to the first axis 310. A person skilled in the art will appreciate that the direction may not be precisely perpendicular but nevertheless be considered to be substantially perpendicular due to any number of factors, such as manufacturing tolerances and sensitivity of measurement equipment.

In the pre-use configuration, the piercing element 324 has not pierced the first seal member 346 or the second seal member 348, and the drug delivery device 300 is ready for use by a user.

During use of the drug delivery device 300, an insertion force above the threshold force is applied to the body 302, and the second body shoulder 352 of the body 302 moves past the ridge 368. The moveable arm 360b is then able to return to its rest position as the body shoulder 352 fits within the recess 370 and, therefore, the body 302 is able to slide within the dispensing head 304 without hindrance from the body shoulder 352.

As the body 302 is inserted further in the proximal direction, the piercing element 324 contacts and then pierces the first seal member 346 so that the distal piercing inlet 326 is within the proximal cavity 338 of the drug holder 336 and the air 340 in the proximal cavity 338 enters the piercing element 324. The air 340 moves proximally in the piercing element 324 and encounters and passes through a spinning nozzle 372, e.g., through perforations formed in the spinning nozzle 372.

Figure 9:
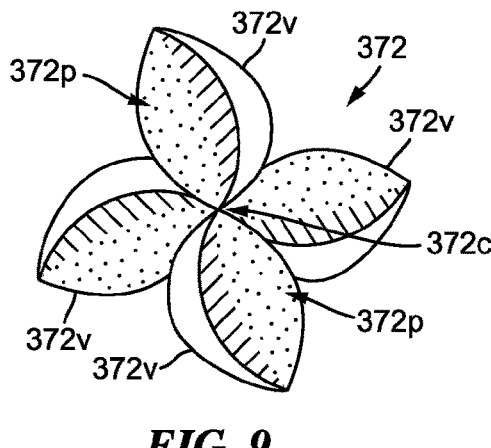
FIG. 9 is a top view of one embodiment of a spinning nozzle.

FIG. 9 illustrates an exemplary embodiment of the spinning nozzle 372. The spinning nozzle 372 is configured as a turbine including a plurality of vanes 372v extending radially outward from a center point 372c that defines a central axis of the spinning nozzle 372. The turbine in this exemplary embodiment is configured as a pinwheel. The central axis is coaxial with the first axis 210 in this illustrated embodiment and defines the axis about which the spinning nozzle 372 is configured to spin, similar to windmill spinning. The turbine includes four vanes 372v in this illustrated embodiment but can include another plural number of vanes 372v. Each of the vanes 372v includes a plurality of perforations 372p therein. The number of perforations 372p is the same in each of the vanes 372v, but in other embodiments one or more of the vanes 372v can have a different number of perforations 372p than one or more of the other vanes 372v. As discussed herein, the spinning nozzle 372 is configured such that air and drug can pass through a spinning nozzle 372, e.g., through the perforations 372p formed in the spinning nozzle 372. Some air and/or drug may pass through a gap of space between adjacent vanes 372v of the spinning nozzle 372. In an exemplary embodiment, as shown in FIG. 9, the vanes 372v can be arranged to partially overlap one another to help prevent air and drug from passing between the vanes 372v and thereby encourage air and drug to instead pass through the perforations 372p.

Referring again to the method of using the drug delivery device 300, the proximal movement of the air 340 causes the spinning nozzle 372 to spin, e.g., rotate, about the first axis 310. The air 340 can be compressed in the proximal cavity 338 prior to the first seal member 346 being broken, which may facilitate proximal traveling of the air 340 and rotation of the spinning nozzle 372. The spinning nozzle 372 can be located anywhere along the flow path of the air 340 that is distal to the opening 316. Further proximal movement of the body 302 causes the piercing element 324 to contact and then pierce the second seal member 348 so that the distal piercing inlet 326 is within the distal cavity 342 of the drug holder 336. The drug 344 in the distal cavity 342 is drawn proximally into the piercing element 324 due to the proximal flow of the air 340. The drug 344 moves proximally in the piercing element 324 and encounters and passes through the spinning nozzle 372, which is spinning due to the air flow therethrough. The spinning of the spinning nozzle 372 causes the drug 344, which is a liquid, to be dispersed as liquid particles of a substantially same size and at a substantially consistent distribution as the drug 344 exits the drug delivery device 300 through the opening 316, as shown in FIG. 8. The size of the liquid particles is defined by a size of each of the perforations 372*p*. A person skilled in the art will appreciate that the liquid particles may not be precisely the same size but nevertheless be considered to be substantially the same size due to any number of factors, such as manufacturing tolerances and sensitivity of measurement equipment. Similarly, a person skilled in the art will appreciate that the liquid particles may not be precisely constantly distributed but nevertheless be considered to be at a substantially constant distribution due to any number of factors, such as manufacturing tolerances and sensitivity of measurement equipment.

Further movement of the body 302 in the proximal direction causes the piercer stop 328 to come into contact with the second seal member 348. The contact between the piercer stop 328 and the second seal member 348 can be configured to prevent further insertion of the body 302 in the proximal direction, which can act as an indicator to a user of the drug delivery device 300 that actuation has been completed. In some embodiments the second seal member 348 may not have sufficient stiffness to allow for contact between the piercer stop 328 and the second seal member 348 to prevent further insertion of the body 302. In such embodiments, the second seal member 348 can be seated in a rigid housing configured to contact the piercer stop 328 instead of the second seal member 328. Whether or not the second seal member 348 has sufficient stiffness to allow for contact between the piercer stop 328 and the second seal member 348 to prevent further insertion of the body 302, and whether or not the second seal member 348 is seated in a rigid housing, the piercing element 324 and the drug holder 336 can be configured to cooperate to prevent further insertion of the body 302. The distal piercing tip 326 can be configured to abut a bottom internal surface of the drug holder 336, e.g., a bottom internal surface of the distal cavity 342, which can be configured to prevent further insertion of the body 302.

During insertion of the body 302 into the dispensing head 304, air trapped within the socket 312 can be expelled through openings 374, which are through finger flanges 376 of the body 302 and into the socket 312 (see FIGS. 4 and 5). The trapped air being expelled through the openings 374 prevents compression of the trapped air, which may alter the insertion force required.

When the body 302 has almost been inserted a second predetermined distance 378, a ramp 380 that precedes the first body shoulder 350 makes contact with the ramp 358 of the head shoulder 354 of the dispensing head 304. The ramps 380, 358 interact as described above with respect to ramp interaction, and when the body 302 is inserted the second predetermined distance 278, the first body shoulder 350 has moved beyond the head shoulder 360 and returned to a rest position thereby preventing withdrawal of the body 302 from the dispensing head 354. Further movement of the body 302 into the dispensing head 304 can be prevented by the endplate 306 or by contact of the peripheral wall 334 with the dispensing head 304. The first body shoulder 350 and the head shoulder 354 are therefore configured to provide an automatically engaging post-lock 382 that retains the drug delivery device 300 in the post use configuration, as shown in FIG. 8.

The drug delivery device 300 in the illustrated embodiment of FIG. 3 is not powered, e.g., does not include any electrical components such as a processor, a sensor, a memory, a communications interface, etc.

Figure 10:
FIG. 10 is a side, partially cross-sectional view of a proximal portion of another embodiment of the drug delivery device of FIG. 1.

FIG. 10 illustrates another exemplary embodiment of the drug delivery device 100 of FIG. 1. This illustrated embodiment of a drug delivery device 500 is generally configured and used similar to the drug delivery device 300 of FIGS. 3 and 4 and is similarly horizontally positioned. However, the drug delivery device's spinning nozzle 502, e.g., the spinning nozzle 372 of FIG. 9, is at a different location. The spinning nozzle 502 is not located in a piercing element 504 but is instead located just proximal to the piercing element 504 and just distal to an opening 506 in a tip 508 of the drug delivery device 500. Also, as shown in FIG. 10, the opening 506 in this illustrated embodiment includes a circular ring-shaped opening that is in fluid communication with a hollow interior 510 of the piercing element 504 through the spinning nozzle 502.

The drug delivery device 500 in the illustrated embodiment of FIG. 10 is not powered, e.g., does not include any electrical components such as a processor, a sensor, a memory, a communications interface, etc.

Figure 11:
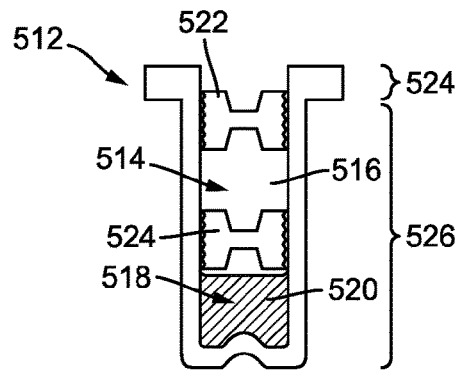
FIG. 11 is a side cross-sectional view of another embodiment of a vial.

FIG. 11 illustrates an exemplary embodiment of a drug holder 512 configured to be used with the drug delivery device 500 of FIG. 10, although the drug holder 512 can be similarly used with other embodiments of drug delivery devices described herein. The drug holder 512 in this illustrated embodiment is a vial and is generally configured and used similar to the drug holder 200 of FIG. 2 and includes a proximal cavity 514 containing air 516 therein, a distal cavity 518 containing a drug 520 therein, a first seal member 522, and a second seal member 524. The drug holder 512 in this illustrated embodiment includes a base portion 526 and a head portion 528 that has a larger maximum outer diameter than then base portion 526, though the drug holder 512 does not include a tapering neck portion. The first and second seal members 522, 524 in this illustrated embodiment each include a stopper.

Embodiments of nasal drug delivery devices disclosed herein can be designed to be disposed of after a single use, or they can be designed to be used multiple times. In either case, in at least some embodiments, the drug delivery device can be reconditioned for reuse after at least one use. Reconditioning can include any combination of the steps of disassembly of the drug delivery device, followed by cleaning or replacement of particular pieces and subsequent reassembly. In particular, the drug delivery device can be disassembled, and any number of the particular pieces or parts of the drug delivery device can be selectively replaced or removed in any combination. Upon cleaning and/or replacement of particular parts, the drug delivery device can be reassembled for subsequent use either at a reconditioning facility, or by a health care provider immediately prior to use. A person skilled in the art will appreciate that reconditioning of a drug delivery device can utilize a variety of techniques for disassembly, cleaning/replacement, and reassembly. Use of such techniques, and the resulting reconditioned drug delivery device, are all within the scope of the present application.

The present disclosure has been described above by way of example only within the context of the overall disclosure provided herein. It will be appreciated that modifications within the spirit and scope of the claims may be made without departing from the overall scope of the present disclosure.

What is claimed is:

1. A drug delivery device, comprising:
   a tip configured to be positioned in a nose of a patient, the tip having an opening therein;

a drug holder with an air chamber, a drug chamber, a first seal member that isolates the air chamber from the opening, and a second seal member that isolates the air chamber from the drug chamber, the air chamber containing air therein, and the drug chamber containing a drug therein;

a turbine located distal to the opening and proximal to the air chamber;

wherein the breaking of the first seal member is configured to cause the air to flow proximally and thereby cause the turbine to spin; and the breaking of the second seal member is configured to cause the drug to be drawn proximally and pass through the turbine and then out of the opening.

2. The device of claim 1, further comprising a piercing element in fluid communication with the opening and configured to break the first seal member and to subsequently break the second seal member.

3. The device of claim 2, wherein the piercing element comprises a tubular needle.

4. The device of claim 3, wherein the turbine is located in a hollow interior of the tubular needle.

5. The device of claim 2, wherein the turbine is located proximal to the piercing element and distal to the opening.

6. The device of claim 2, further comprising an actuator configured to be actuated to cause the piercing element to break the first seal member and subsequently break the second seal member.

7. The device of claim 6, further comprising a dispensing head that includes the tip; wherein the actuator includes a body that seats the drug holder therein and that is seated in a socket of the dispensing head.

8. The device of claim 1, wherein the turbine includes a plurality of vanes extending radially outward from a center point of the turbine, perforations are formed in the plurality of vanes, the drug is configured pass through the perforations, and the turbine is configured to spin about the center point.

9. The device of claim 1, wherein the turbine includes a pinwheel.

10. The device of claim 1, wherein the drug holder includes a vial.

11. The device of claim 1, wherein the drug is one of ketamine, esketamine, naloxone, and sumatriptan.

12. A drug delivery device, comprising:

a tip configured to be positioned in a nose of a patient, the tip having an opening therein;

an air chamber containing air therein;

a nozzle located distal to the opening and proximal to the air chamber, the nozzle including a plurality of perforations therethrough;

a first seal member located between the air chamber and the opening and providing a seal therebetween;

a drug chamber containing a drug therein and located distal to the air chamber;

a second seal member located between the air chamber and the drug chamber and providing a seal therebetween; and an actuator configured to be actuated to cause the first seal member to break and subsequently cause the second seal member to break;

wherein the breaking of the first seal member is configured to cause the air to flow proximally and thereby cause the nozzle to spin; and the breaking of the second seal member is configured to cause the drug to be drawn proximally and pass through the plurality of perforations and then out of the opening.

13. The device of claim 12, further comprising a piercing element in fluid communication with the opening and configured to, in response to the actuation of the actuator, break the first seal member and to subsequently break the second seal member.

14. The device of claim 13, wherein the piercing element comprises a tubular needle.

15. The device of claim 14, wherein the nozzle is located in a hollow interior of the tubular needle.

16. The device of claim 13, wherein the nozzle is located proximal to the piercing element and distal to the opening.

17. The device of claim 12, further comprising a dispensing head that includes the tip; wherein the actuator includes a body that is seated in a socket of the dispensing head.

18. The device of claim 12, wherein the nozzle includes a plurality of vanes extending radially outward from a center point of the nozzle, the plurality of perforations are formed in the plurality of vanes, and the nozzle is configured to spin about the center point.

19. The device of claim 12, wherein the drug is one of ketamine, esketamine, naloxone, and sumatriptan.

20. A drug delivery method, comprising:

breaking a first seal member of a nasal drug delivery device and thereby causing air located in the drug delivery device to flow proximally, the proximal flow of the air causing a turbine of the drug delivery device to spin; and after breaking the first seal member and after the turbine has begun to spin, breaking a second seal member of the drug delivery device and thereby causing a drug to be drawn proximally by the proximal flow of the air, to then pass through the spinning turbine, and to then exit the drug delivery device through an opening in the drug delivery device.

21. The method of claim 20, wherein a drug holder includes an air chamber located distal to the first seal member and proximal to the second seal member such that breaking the first seal member allows air in the air chamber to flow proximally, and the drug holder includes a drug chamber located distal to the second seal member such that breaking the second seal member allows drug in the drug chamber to be drawn proximally.

22. The method of claim 21, wherein the drug holder includes a vial.

23. The method of claim 20, wherein a piercing element of the drug delivery device breaks the first seal member and subsequently breaks the second seal member.

24. The method of claim 23, wherein the air flowing proximally passes through a hollow interior of the piercing element.

25. The method of claim 24, wherein the air flowing proximally passes through perforations formed in the turbine before exiting the hollow interior of the piercing element.

26. The method of claim 25, wherein the air flowing proximally exits the hollow interior of the piercing element before passing through the perforations of the turbine.

27. The method of claim 20, wherein breaking the first seal member and breaking the second seal member includes actuating an actuator of the drug delivery device.

28. The method of claim 27, wherein the actuator includes a body of the drug delivery device that is seated in a socket of a dispensing head of the drug delivery device.

29. The method of claim 20, wherein the turbine includes a pinwheel.

30. The method of claim 20, wherein the drug is one of ketamine, esketamine, naloxone, and sumatriptan.

\* \* \* \* \*